US008832763B2

(12) United States Patent
Kalidindi et al.

(10) Patent No.: US 8,832,763 B2
(45) Date of Patent: Sep. 9, 2014

(54) CATALOG SLICING IN A VIDEO PROVISIONING SYSTEM

(75) Inventors: Srirama R. Kalidindi, Flower Mound, TX (US); Sanjay Ahuja, Irving, TX (US); Xuejun Hu, Coppell, TX (US); Tulasi Kumar Neeli, Irving, TX (US); Mukunda P. Raju, Irving, TX (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 271 days.

(21) Appl. No.: 13/196,760

(22) Filed: Aug. 2, 2011

(65) Prior Publication Data

US 2012/0079546 A1 Mar. 29, 2012

Related U.S. Application Data

(60) Provisional application No. 61/387,939, filed on Sep. 29, 2010.

(51) Int. Cl.
| | | |
|---|---|---|
| *H04N 7/173* | (2011.01) | |
| *H04N 5/445* | (2011.01) | |
| *A61N 5/06* | (2006.01) | |
| *H04N 21/472* | (2011.01) | |
| *H04N 21/2668* | (2011.01) | |
| *H04N 21/258* | (2011.01) | |
| *H04N 21/431* | (2011.01) | |
| *H04N 21/475* | (2011.01) | |
| *H04N 21/8549* | (2011.01) | |
| *H04N 21/2225* | (2011.01) | |
| *H04N 21/84* | (2011.01) | |

(52) U.S. Cl.
CPC ........ *A61N 5/0618* (2013.01); *H04N 21/47202* (2013.01); *H04N 21/2668* (2013.01); *H04N 21/25891* (2013.01); *H04N 21/4316* (2013.01); *H04N 21/4755* (2013.01); *H04N 21/8549* (2013.01); *H04N 21/2225* (2013.01); *H04N 21/84* (2013.01)
USPC .............. 725/115; 725/39; 725/110; 725/116

(58) Field of Classification Search
USPC .................................... 725/110, 39, 115–116
See application file for complete search history.

(56) References Cited

U.S. PATENT DOCUMENTS

| | | | |
|---|---|---|---|
| 7,191,189 B2 * | 3/2007 | Bhatti ................................. 1/1 |
| 2004/0133855 A1 * | 7/2004 | Blair et al. ..................... 715/517 |
| 2004/0177319 A1 * | 9/2004 | Horn ........................... 715/501.1 |
| 2005/0172318 A1 * | 8/2005 | Dudkiewicz et al. ........... 725/46 |
| 2007/0245367 A1 * | 10/2007 | Ogawa ............................ 725/28 |
| 2009/0031392 A1 * | 1/2009 | VerSteeg et al. ............... 725/151 |

\* cited by examiner

*Primary Examiner* — Jason J Chung
*Assistant Examiner* — Sumaiya A Chowdhury

(57) ABSTRACT

A system, associated with a video provisioning system, may receive a hierarchical representation of categories and subcategories associated with a catalog of video assets; and condense the hierarchical representation of categories and subcategories into a file. The system may further transmit the file to a set top box, where transmitting the file allows the set top box to access the hierarchical representation of categories and subcategories without retrieving, from the video provisioning system, additional information associated with the hierarchical representation of categories and subcategories.

25 Claims, 7 Drawing Sheets

CATALOG SLICING IN A VIDEO PROVISIONING SYSTEM

REFERENCE TO RELATED APPLICATION

This application claims priority to U.S. Provisional Patent Application No. 61/387,939, filed Sep. 29, 2010, the entire contents of the provisional application being incorporated herein by reference.

BACKGROUND

Users, of user devices, have a growing array of sources, networks, and/or content providers from which to obtain video content and/or services. The users may use video client devices (e.g., a set top box, etc.) to obtain free broadcast television video content (e.g., from Fox, ABC, CBS, etc.), on-demand video content (e.g., Video On-Demand (VOD), pay-per-view (PPV), etc.), and/or pay television video content (e.g., from HBO, Cinemax, etc.) from cable television operators (e.g., Comcast, Time Warner, etc.) and/or satellite television operators (e.g., DirectTV, Dish Network, etc.). The users may use computer devices, wireless mobile handset devices, etc. to obtain other video content from on-line content providers, such as television operators (e.g., ABC, Fox, CBS, etc.), over-the-top (OTT) content providers (e.g., Hulu, Veoh, Jaman, YouTube, etc.), and/or other commercial content providers (e.g., Apple Computer's iTunes, Netflix, Blockbuster, etc.).

A user device may access a catalog that contains information associated with video assets that are available to be downloaded from a network. The user device may navigate through folders and/or subfolders within the catalog to select a particular video asset to download. The user device may send, to the network, a request for catalog information each time the user navigates to a different folder and/or subfolder. The quantity of time associated with sending the request and/or receiving the catalog information may cause the user, of the user device, to wait before navigating to another folder and/or subfolder.

DETAILED DESCRIPTION OF PREFERRED EMBODIMENTS

Figure 1:
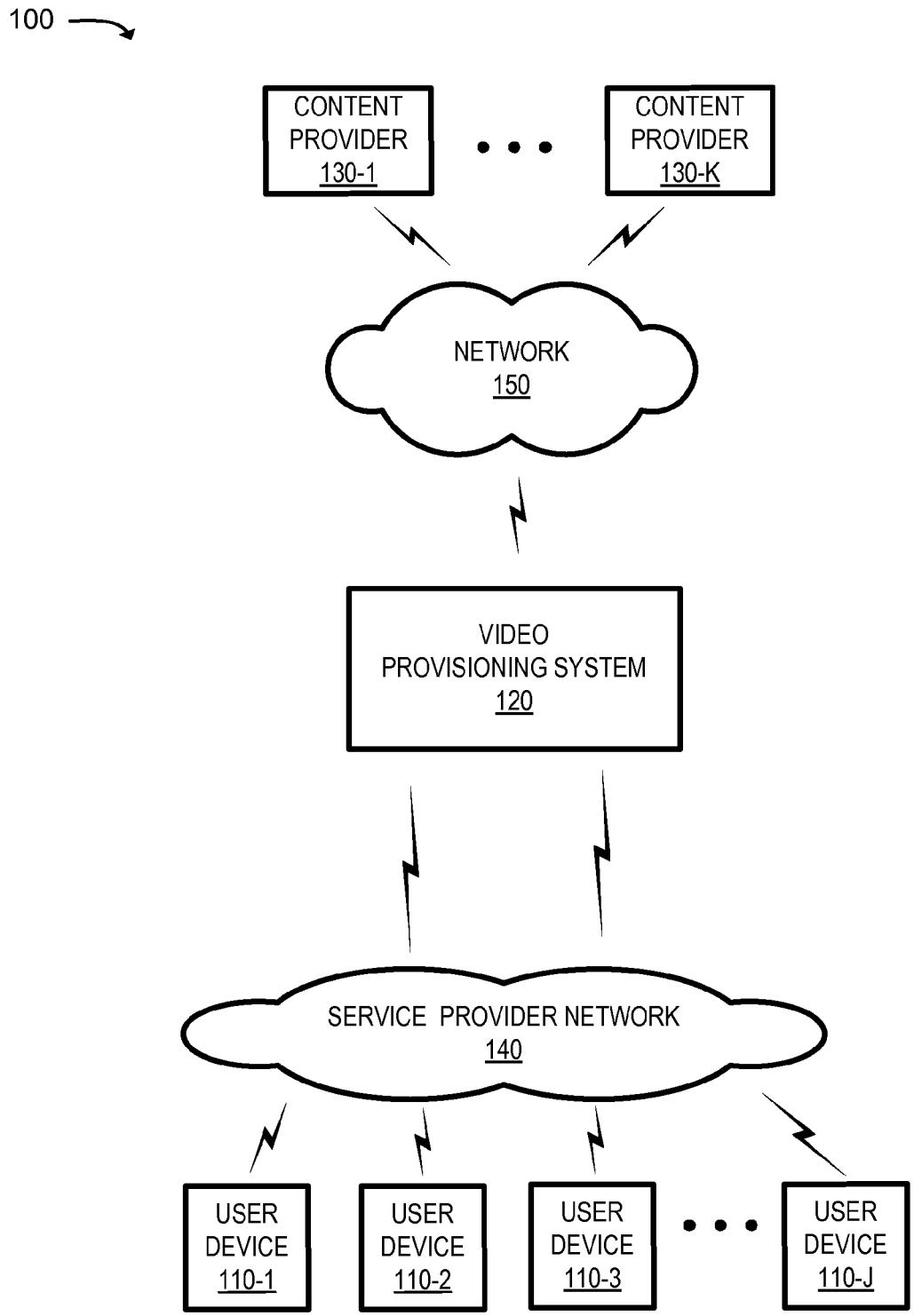
FIG. 1 is a diagram of an example environment in which the systems and/or methods, described herein, may be implemented.

The following detailed description refers to the accompanying drawings. The same reference numbers in different drawings may identify the same or similar elements.

Systems and/or methods, described herein, may allow a user device to navigate via a hierarchical data structure, associated with a catalog of video assets that are stored within a video provisioning system, without making data calls for additional information each time a different portion of the data structure is accessed. Enabling the user device to navigate through the data structure, without performing the data calls, may reduce a quantity of time and/or bandwidth utilization associated with rendering the data structure, on the user device, which may improve a user experience for a user of the user device.

The hierarchical data structure, as described herein, may represent the catalog, of video assets, as a multilevel set of files and/or folders, subfolders, etc. that correspond to a variety of categories, subcategories, genres, subgenres, content providers, etc. included in the catalog of video assets. In other implementations, any type of hierarchical data structure may be used to represent the categories, subcategories, genres, subgenres, content providers, etc. associated with the catalog of video assets. Thus, the hierarchical data structure, as described herein, is provided for explanatory purposes only.

The systems and/or methods may enable information associated with the catalog (hereinafter referred to as "catalog information"), to be processed and/or apportioned between one or more files (referred to, herein, as "condensed files"). A first portion of the catalog information (hereinafter referred to as "folder information") may include information that corresponds to folders and/or subfolders, associated with a hierarchical data structure of the catalog, that do not contain metadata associated with video assets (e.g., such as titles, etc.). The folder information may be processed and/or stored in a condensed file. A second portion of the catalog information may correspond to metadata, associated with video assets. The metadata may be associated with one or more leaf folders identified within the folder information. The metadata may be stored in one or more child condensed files associated with the leaf folders.

The systems and/or methods may cause the folder information to be converted and/or compressed into a format that can be stored, as the condensed file, within a memory associated with the user device. Storing the condensed file, within the memory, allows the user device to use the condensed file to navigate through the folders and/or subfolders without repeatedly requesting additional catalog information. The user device may navigate to a folder or subfolder that includes a leaf folder and a user of the user device may instruct the user device to select the leaf folder. The user device may, based on the selection of the leaf folder, retrieve the child condensed file, from the network, that corresponds to the selected leaf folder. The user device may obtain, from the child condensed file, metadata associated with a video asset and may use the metadata to obtain the video asset.

FIG. 1 is a diagram of an example environment in which the systems and/or methods, described herein, may be implemented. As shown in FIG. 1, environment 100 may include a group of user devices 110-1, . . . , 110-J (where J≥1) (hereinafter referred to collectively as "user devices 110" and individually as "user device 110"), a video provisioning system (VPS) 120, a group of content providers 130-1, . . . , 130-K (where K≥1) (hereinafter referred to collectively as "content providers 130" and individually as "content provider 130"), a service provider network 140, and a network 150. The number of devices, systems, and/or networks, illustrated in FIG. 1, is provided for explanatory purposes only. In practice, there may be additional devices, systems, and/or networks; fewer devices, systems, and/or networks; different devices, systems, and/or networks; or differently arranged devices, systems, and/or networks than illustrated in FIG. 1.

Also, in some implementations, one or more of the devices of environment 100 may perform one or more functions described as being performed by another one or more of the devices of environment 100. Devices, systems, and/or networks of environment 100 may interconnect via wired connections, wireless connections, or a combination of wired and wireless connections.

User device 110 may include a computation or communication device that is capable of communicating with service provider network 140. For example, user device 110 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a laptop computer, a tablet computer, a set top box, a digital video recorder (DVR), a personal gaming system, a smart phone, or another type of computation or communication device.

User device 110 may communicate with VPS 120 and/or perform certain operations to obtain a video asset from VPS 120. For example, user device 110 may access a store front (e.g., a website, a user interface, an interactive program guide (IPG), an interactive media guide (IMG), etc.) associated with VPS 120, to browse, search, select, and/or obtain a video asset.

User device 110 may, for example, retrieve a condensed file, from VPS 120, that includes folder information that can be stored in a memory associated with user device 110. User device 110 may display the folder information as a series of folders and/or subfolders via which user device 110 may navigate without repeatedly retrieving additional folder information each time a different folder and/or subfolder is accessed by user device 110. When user device 110 accesses a folder or subfolder and selects a leaf folder, user device 110 may communicate, with VPS 120, to obtain a child condensed file that corresponds to the selected leaf folder. User device 110 may open the child condensed file to obtain metadata, such as, for example, titles associated with one or more video assets. User device 110 may select a title, associated with a particular video asset. User device 110 may retrieve the particular video asset, form VPS 120, for display on user device 110.

VPS 120 may include one or more devices that gather, process, search, store, and/or provide information in a manner similar to that described herein. VPS 120 may be capable of communicating with content providers 130 via network 150 and/or user devices 110 via service provider network 140. VPS 120 may provide a video provisioning service to user devices 110.

VPS 120 may, for example, perform operations associated with video content ingestion, processing, and/or distribution for one or more types of user devices 110, associated with a user, within environment 100. The video content may include a video asset and/or metadata associated with the video asset. VPS 120 may communicate with one or more content providers 130 to acquire video content. VPS 120 may connect to a collection of different types user devices 110 associated with a user, such as, for example, a set top box, a computer device, a wireless handheld device, and/or other types of user devices 110. VPS 120 may connect to the set top box via a television service provider network 140 (e.g., a cable television network, a satellite television network, a fiber optic television network, or some combination thereof). VPS 120 may connect to the computer device via a broad band service provider network 140 (e.g., via the Internet). VPS 120 may connect to the wireless handset device via a wireless service provider network 140. VPS 120 may perform an ingestion operation on the acquired video content. VPS 120 may process and/or publish the ingested video content in a manner that allows the video content to be offered and/or distributed to the different types of user devices 110.

VPS 120 may generate a catalog that can be used, by user device 110, to select and/or obtain a video asset. VPS 120 may store folder information associated with the catalog structure (e.g., folders, selected subfolders, etc.) in a condensed file to be distributed to user device 110. VPS 120 may store metadata, associated with video assets, in one or more child condensed files that are associated with the condensed file. VPS 120 may distribute a child condensed file when requested by user device 110.

Content provider 130 may include any type or form of content provider. For example, content provider 130 may include free television broadcast providers (e.g., local broadcast providers, such as NBC, CBS, ABC, and/or Fox), for-pay television broadcast providers (e.g., TNT, ESPN, HBO, Cinemax, CNN, etc.), and/or Internet-based content providers (e.g., Youtube, Vimeo, Netflix, Hulu, Veoh, etc.) that stream content from web sites and/or permit content to be downloaded (e.g., via progressive download, etc.). Content provider 130 may include on-demand content providers (e.g., video on demand (VOD), pay per view (PPV), etc.). A media stream, as used herein, may refer to a stream of content that includes video content (e.g., a video stream), audio content (e.g., an audio stream), and/or textual content (e.g., a textual stream).

The term video asset, as used herein, may include VOD content, pay-per-view (PPV) video content, rented video content, free television content (e.g., from free television broadcasters, etc.), paid for television content (e.g., from pay television content providers), on-line video content (e.g., on-line television programs, movies, videos, etc.), advertising, games, music videos, promotional information (e.g., such as previews, trailers, etc.), etc. A video asset may be stored in one or more video files that contain video information that can be played on a user device.

Content provider may provide metadata associated with video assets. The metadata may describe the video asset and/or may enable the video asset to be processed, stored, managed, offered, and/or distributed to user device 110. Content provider 130 may, in another example, provide metadata, associated with video assets that are not yet available for distribution to user devices 110. The metadata may identify a date when the video assets can be made available and/or distributed to user devices 110.

Service provider network 140 may include one or more wired and/or wireless networks via which user devices 110 communicate with and/or receive video content from VPS 120. For example, service provider network 140 may include a cellular network, the Public Land Mobile Network (PLMN), a second generation (2G) network, a third generation (3G) network, a fourth generation (4G) network (e.g., a long term evolution (LTE) network), a fifth generation (5G) network, and/or another network. Additionally, or alternatively, service provider network 140 may include a code division multiple access (CDMA) network, a global system for mobile communications (GSM) network, a general packet radio services (GPRS) network, or a combination of CDMA, GSM, and/or GPRS networks. Additionally, or alternatively, service provider network 140 may include a wide area network (WAN), a metropolitan area network (MAN), an ad hoc network, an intranet, a fiber optic-based network (e.g., a fiber optic service (FiOS) network), a television network, and/or a combination of these or other types of networks.

Network 150 may include one or more wired and/or wireless networks. For example, network 150 may include a cellular network, the PLMN, a 2G network, a 3G network, a 4G network (e.g., an LTE network), a 5G network, and/or another network. Additionally, or alternatively, network 150 may include a WAN, a MAN, a telephone network (e.g., the Public Switched Telephone Network (PSTN)), an ad hoc network, an intranet, the Internet, a fiber optic-based network, and/or a combination of these or other types of networks.

Figure 2:
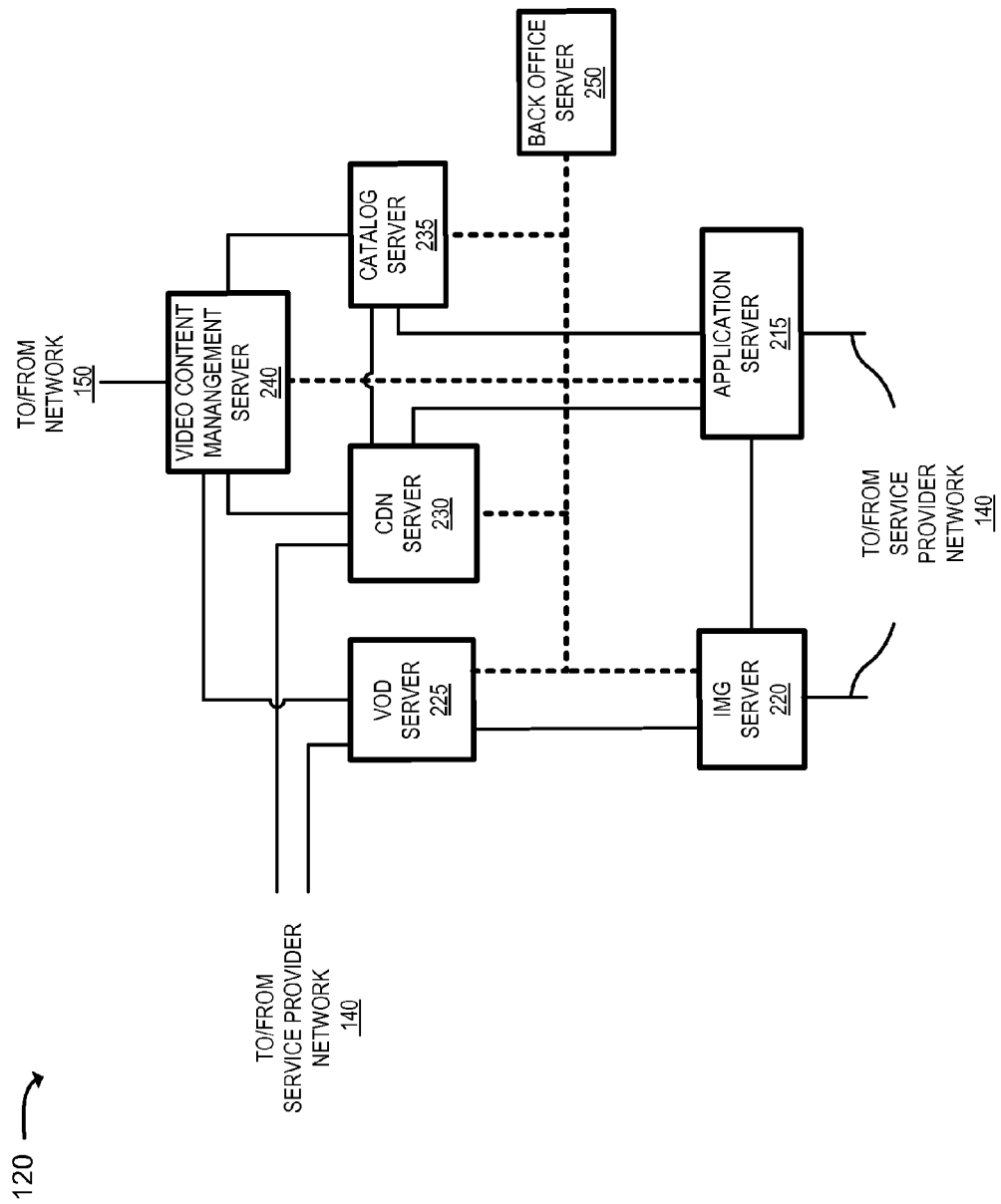
FIG. 2 is a diagram of example devices, associated with the video provisioning system, of FIG. 1.

FIG. 2 is a diagram of example devices associated with VPS 120. VPS 120 may include an application server 215, an interactive media guide (IMG) server 220, a video on-demand (VOD) server 225, a content delivery network (CDN) server 230, a catalog server 235, a video content management (VCM) server 240, and a back office server 250 (hereinafter referred to as "BOS 250"). Although FIG. 2 shows example devices of VPS 120, in other implementations, VPS 120 may include fewer devices, additional devices, different devices, or differently arranged devices than depicted in FIG. 2. Additionally, or alternatively, one or more devices of VPS 120 may perform one or more tasks described as being performed by one or more other devices of VPS 120.

In the description below, VOD server 225 is described as provisioning video services for a type of user device 110 (i.e., a set top box) and CDN server 230 is described as provisioning video services for another type of user device 110 (i.e., a computer device, a wireless handset device, etc.) for explanatory purposes. In another implementation, the video services may be provisioned for the set top box and/or the other types of user devices 110 in a number of ways. For example, VOD server 225 and/or CDN server 230 may be combined into a single device that provisions the video services for each type of user device 110. In another example, the video services may be provisioned, for each type of user device 110, by another device and/or network instead of, or in combination with, VOD server 225 and/or CDN server 230. Additionally, IMG server 220 is described as providing an a store front (i.e., via an IMG), that can be accessed by the set top box, and application server 215 is described as providing another store front (e.g., via a web page, a user interface, an interactive program guide, etc.), that can be accessed by the other types of user devices 110, for explanatory purposes. In another implementation, the store front may be provisioned for the set top box and/or the other types of user devices 110 in a number of ways. For example, IMG server 220 and/or application server 215 may be combined into a single device that provisions the store front for each type of user device 110. In another example, the store front may be provisioned, for each type of user device 110, by another device and/or network instead of, or in combination with, IMG server 220 and/or application server 215. Thus, the examples below are provided for explanatory purposes only.

Application server 215 may include one or more server devices, or other types of computation or communication devices, that gather, process, search, store, and/or provide information in a manner similar to that described herein. Application server 215 may receive metadata that has been published by catalog server 235. The metadata may, in one example, be associated with video assets that are stored in CDN server 230.

Application server 215 may host a store front (e.g., a VPS store front), such as a private website (e.g., for subscribing user devices 110), a public website (e.g., for non-subscribing user devices 110), a user interface (UI) (e.g., that is accessible by wireless handset user devices 110, etc.), an interactive program guide (e.g., an IMG for set top box-type user devices 110) and/or other types of user interfaces. The store front may enable single sign-on (SSO) store front access, to a user of one or more user devices 110, based on the same login credentials (e.g., username, password, personal identification number (PIN), etc.). Application server 215 may publish all or a portion of the metadata, associated with the video assets, to the store front that permits any of user devices 110 to browse, perform searches, process payment, etc. for video assets based on the metadata that is published to the store front.

Application server 215 may store information associated with a transaction history that corresponds to a type of user device 110 (e.g., a computer user device 110, a wireless handheld user device 110, a gaming user device 110, etc.) that is different than a set top box user device 110. The transaction history may include information regarding prior transactions (e.g., purchases, rentals, subscriptions, etc.), associated with one or more video assets, by user device 110. The transaction history may also identify a period of time during which a rental period or subscription period, for a video asset, is valid.

Application server 215 may transmit, to user device 110, folder information (e.g., as a condensed file) received from BOS 250. Application server 215 may receive, from user device 110, a request for a child condensed file that corresponds to a leaf folder included within the folder information. Application server 215 may receive the request and may obtain, from BOS 250, the child condensed file. Application server 215 may transmit the child condensed file, to user device 110, in response to the request.

IMG server 220 may include one or more server devices, or other types of computation or communication devices, that gather, process, search, store, and/or provide information in a manner similar to that described herein. IMG server 220 may, for example, process metadata, that has been published by catalog server 235 and/or VOD server 225, in a manner similar to that described above (e.g., with respect to application server 215). The metadata may be associated with video assets that are stored in VOD server 225. The metadata may be accessed and/or obtained, via IMG server 220, by a particular type of user device 110, such as a set top box user device 110.

IMG server 220 may publish all or a portion of the metadata, associated with the video assets, to an IMG UI that the set top box user device 110, associated with the user, may render for display on a video display device. IMG server 220 may permit the set top box user device 110 to access information associated with video assets that stored by VOD server 225.

IMG server 220 may store information associated with a transaction history that corresponds to a set top box user device 110. The transaction history may include information regarding prior transactions (e.g., purchases, rentals, subscriptions, etc.), associated with one or more video assets, by set top box user device 110. The transaction history may also identify a period of time during which a rental period or subscription period, for a video asset, is valid.

IMG server 220 may transmit, to set top box user device 110, folder information (e.g., as a condensed file) received from BOS 250. IMG server 220 may receive a request, from set top box user device 110, for a child condensed file that corresponds to a leaf folder included within the catalog information. IMG server 220 may receive the request and may obtain, from BOS 250, the child condensed file. IMG server 220 may transmit the child condensed file, to set top box user device 110, in response to the request.

VOD server 225 may include one or more server devices, or other types of computation or communication devices, that gather, process, search, store, and/or provide information in a manner similar to that described herein. VOD server 225 may, for example, perform operations to receive, store, process, and/or distribute video content in a format that is supported by set top box user devices 110.

VOD server 225 may receive published video assets and/or metadata from VCM server 240. VOD server 225 may store the published video assets in a memory associated with VOD server 225. VOD server 225 may publish the metadata, associated with video assets (e.g., that are available for release), to IMG server 220. In another example implementation, VOD server 225 may communicate with content provider 130 to receive video content directly from content provider 130 (e.g., not via VCM server 240).

VOD server 225 may generate folder information that defines a catalog structure, which includes folders and/or subfolders, via which a set top box user device 110 can navigate, to identify and/or obtain a metadata associated with a video asset stored in VOD server 225. The catalog structure may include a root folder that set top box user device 110 may open to access one or more other folders associated with the catalog. The other folders may be associated with a category, genre, content provider 130, rating, etc. associated with the video assets. The other folders may enable set top box user device 110 to access one or more subfolders that correspond to more specific categories (e.g., subcategories), genres (e.g., subgenres), etc. A folder and/or subfolder may be a leaf folder that may include an indication that set top box user device 110 is to obtain a child condensed file (e.g., that stores metadata) that corresponds to the leaf folder. In another example implementation, IMG server 220 may communicate with VOD server 225 and may generate the catalog information.

CDN server 230 may include one or more server devices, or other types of computation or communication devices, that gather, process, search, store, and/or provide information in a manner similar to that described herein. CDN server 230 may, for example, perform operations to receive, store, process, and/or distribute video content in a format that is supported by one or more types of user devices 110 (e.g., a computer device, a wireless mobile device, a gaming device, etc.) other than, or in addition to, a set top box user device 110. CDN server 230 may actually represent a content delivery network that includes multiple routing and/or storage devices.

CDN server 230 may receive published video assets in multiple video formats from VCM server 240. CDN server 230 may store the published video assets in a memory associated with CDN server 230. CDN server 230 may identify a respective storage location and/or URL for each format of each video asset that are stored within the memory and may send information associated with the storage locations and/or the URLs to catalog server 235. CDN server 230 may provide video assets to wireless handset user devices 110 via a wireless service provider network 140. CDN server 230 may provide the video assets to a computer user device 110 via a broadband service provider network 140 (e.g., the Internet). In another example implementation, CDN server 230 may provide the video assets to a set top box user device 110 via a television service provider network 140 and/or via VOD server 225.

Catalog server 235 may include one or more server devices, or other types of computation or communication devices, that gather, process, search, store, and/or provide information in a manner similar to that described herein. Catalog server 235 may, for example, receive, from VCM server 240, published metadata associated with video assets that have been published to VOD server 225 and/or CDN server 230. Catalog server 235 may identify, from the metadata, information associated with the availability of the video assets based on dates on which the video assets are released, blacked out, etc. Catalog server 235 may process and/or package the metadata in order to offer, to user devices 110, the video assets to which the metadata corresponds. The processed metadata associated with the video assets may include identifiers (e.g., video asset numbers, titles, etc.), availability dates, prices (e.g., sale prices, rental prices, subscription prices, etc.), cover art (e.g., images, trailers, etc.), descriptions (e.g., a synopsis, a summary, etc. of the video assets), ratings, reviews, genres, casting information (e.g., actors, directors, producers, etc.), etc. Catalog server 235 may, for example, publish the metadata to the store front associated with application server 215.

Catalog server 235 may generate folder information that defines a catalog structure, which includes folders and/or subfolders, via which user device 110 (e.g., a computer user device 110, a wireless handheld user device 110, a gaming user device 110, etc.) can navigate, to identify and/or obtain metadata associated with a video asset stored in CDN server 230. The catalog structure may include a root folder that user device 110 may access one or more other folders associated with the catalog. The other folders may be associated with a category, genre, content provider 130, rating, etc. associated with video assets. The other folders may enable user device 110 to access one or more subfolders that correspond to more specific categories (e.g., subcategories), genres (e.g., subgenres), etc. A folder and/or subfolder may be a leaf folder that includes an indication that user device 110 is to obtain a child condensed file to obtain metadata (e.g., titles) associated with one or more video assets. In another example implementation, application server 215 may communicate with catalog server 235 and may generate the catalog information.

VCM server 240 may include one or more server devices, or other types of computation or communication devices, that gather, process, search, store, and/or provide information in a manner similar to that described herein. VCM server 240 may, for example, communicate with content providers 130 to ingest video assets to be processed by VPS 120. VCM server 240 may process the video assets to generate copies of the video assets in one or more formats that are supported (e.g., that can be received, processed, and/or played) by the different types of user devices 210. VCM server 240 may publish the one or more formats, associated with the processed video assets, to VOD server 225 and/or CDN server 230.

VCM server 240 may also ingest, process, and/or publish metadata associated with the video assets. VCM server 240 may process the metadata to ensure that the metadata is supported by the different types of user devices 210. VCM server 240 may publish the processed metadata to catalog server 235 and/or VOD server 225.

BOS 250 may include one or more server devices, or other types of computation or communication devices, that gather, process, search, store, and/or provide information in a manner similar to that described herein. BOS 250 may communicate with catalog server 235 and/or VOD server 225 to perform a catalog slicing operation. BOS 250 may, for example, obtain catalog information, from catalog server 235, associated with video assets that are stored in CDN server 230. BOS 250 may, in another example, obtain other catalog information, from VOD server 225, associated with video assets that are stored in VOD server 225. BOS 250 may obtain updated catalog information and/or the other catalog information based on a time interval (e.g., every 12 hours, 24 hours, 48 hours, etc.) and/or upon the occurrence of some event, such as when a video asset is added to and/or removed from VOD server 225 and/or CDN server 230, etc.

BOS 250 may obtain, from the catalog information, folder information that identifies one or more folders and/or subfolders that do not contain metadata associated with video assets. BOS 250 may process the folder information and may store the processed folder information in a condensed file. When processing the folder information, BOS 250 may, for example, compress the folder information from a first size (e.g., based on a quantity of bits) to a second size that is smaller than the first size. The second size may be less than a threshold that corresponds to a memory allocation associated with user device 110. In another example, BOS 250 may convert the folder information, to another format, such as, for example, a binary format, that is more compact (e.g., smaller in size) than a format in which the folder information was received. BOS 250 may transmit the condensed file, to user device 110, via application server 215.

BOS 250 may create another condensed file, using the folder information, obtained from the other catalog information, in a manner similar to that described above. The other folder information may be processed to a third size that is less than another threshold that corresponds to another memory allocation associated with the set top box user device 110. BOS 250 may transmit the other condensed file, to the set top box user device 110, via IMG server 220.

BOS 250 may obtain, from the catalog information, metadata that is associated with a leaf folder, that is identified by the folder information. The leaf folder may store an indication that the metadata is to be obtained from a child condensed file associated with the leaf folder. BOS 250 may generate one or more child condensed files that correspond to the leaf folders identified by the folder information. BOS 250 may, for example, store metadata, that is associated with a leaf folder, in a child condensed file that corresponds to the leaf folder. In another example, BOS 250 may process the metadata prior to storing the metadata in the child condensed file. BOS 250 may, for example, compress all or a portion of the metadata from a first size (e.g., based on a quantity of bits) to a second size that is smaller than the first size. The second size may be less than a threshold that corresponds to a memory allocation associated with user device 110. BOS 250 may process other metadata, obtained from the other catalog information, in a manner similar to that described above. BOS 250 may also generate another one or more child condensed files that correspond to leaf folders identified by the other folder information in a manner similar to that described above.

BOS 250 may transmit a child condensed file, to user device 110 and via application server 215, when BOS 250 receives a request, from user device 110, for the child condensed file. BOS 250 may transmit another condensed file, to the set top box user device 110 and via IMG server 220, when BOS 250 receives a request, from set top box user device 110, for the other child condensed file.

Figure 3:
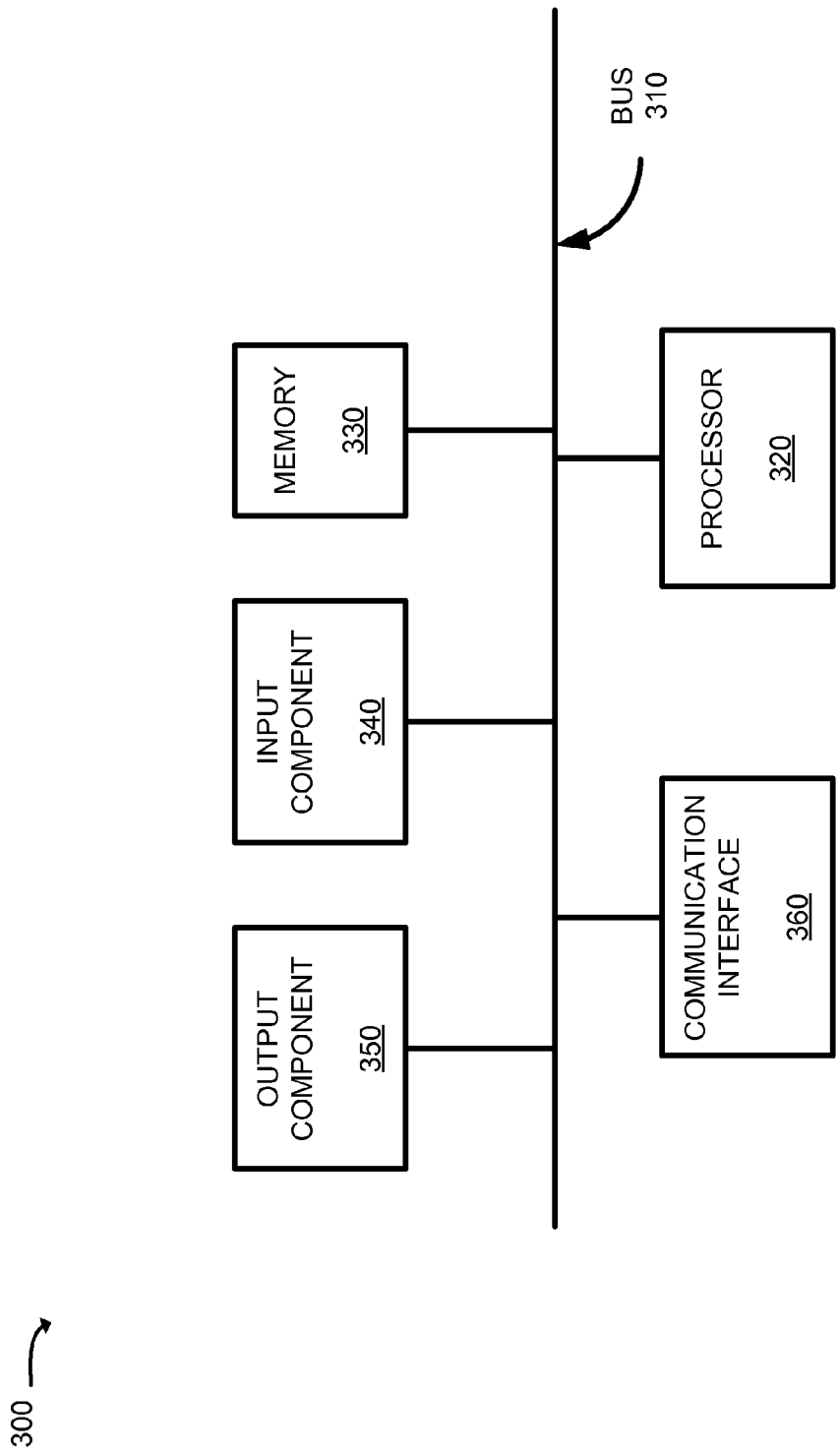
FIG. 3 is a diagram of example components that correspond to one or more of the devices of FIGS. 2 and/or 3.

FIG. 3 is a diagram of example components of a device 300 that may correspond to user device 110, content provider 130, application server 215, IMG server 220, VOD server 225, CDN server 230, catalog server 235, VCM server 240, and/or BOS 250. Alternatively, each of user device 110, content provider 130, application server 215, IMG server 220, VOD server 225, CDN server 230, catalog server 235, VCM server 240, and/or BOS 250 may include one or more devices 300. Device 300 may include a bus 310, a processor 320, a memory 330, an input component 340, an output component 350, and a communication interface 360. Although FIG. 3 shows example components of device 300, in other implementations, device 300 may contain fewer components, additional components, different components, or differently arranged components than depicted in FIG. 3. For example, device 300 may include one or more switch fabrics instead of, or in addition to, bus 310. Additionally, or alternatively, one or more components of device 300 may perform one or more tasks described as being performed by one or more other components of device 300.

Bus 310 may include a path that permits communication among the components of device 300. Processor 320 may include a processor, microprocessor, or processing logic that may interpret and execute instructions. Memory 330 may include any type of dynamic storage device that may store information and instructions, for execution by processor 320, and/or any type of non-volatile storage device that may store information for use by processor 320.

Input component 340 may include a mechanism that permits a user to input information to device 300, such as a keyboard, a keypad, a button, a switch, etc. Output component 350 may include a mechanism that outputs information to the user, such as a display, a speaker, one or more light emitting diodes (LEDs), etc. Communication interface 360 may include any transceiver-like mechanism that enables device 300 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. For example, communication interface 360 may include mechanisms for communicating with another device or system via a network, such as service provider network 140 and/or network 150. In one alternative implementation, communication interface 360 may be a logical component that includes input and output ports, input and output systems, and/or other input and output components that facilitate the transmission of data to other devices.

As will be described in detail below, device 300 may perform certain operations relating to catalog slicing within a video provisioning system. Device 300 may perform these operations in response to processor 320 executing software instructions contained in a computer-readable medium, such as memory 330. A computer-readable medium may be defined as a non-transitory memory device. A memory device may include space within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of or in combination with software instructions to implement processes described herein. Thus, implementations described herein are not limited to any specific combination of hardware circuitry and software.

Figure 4:
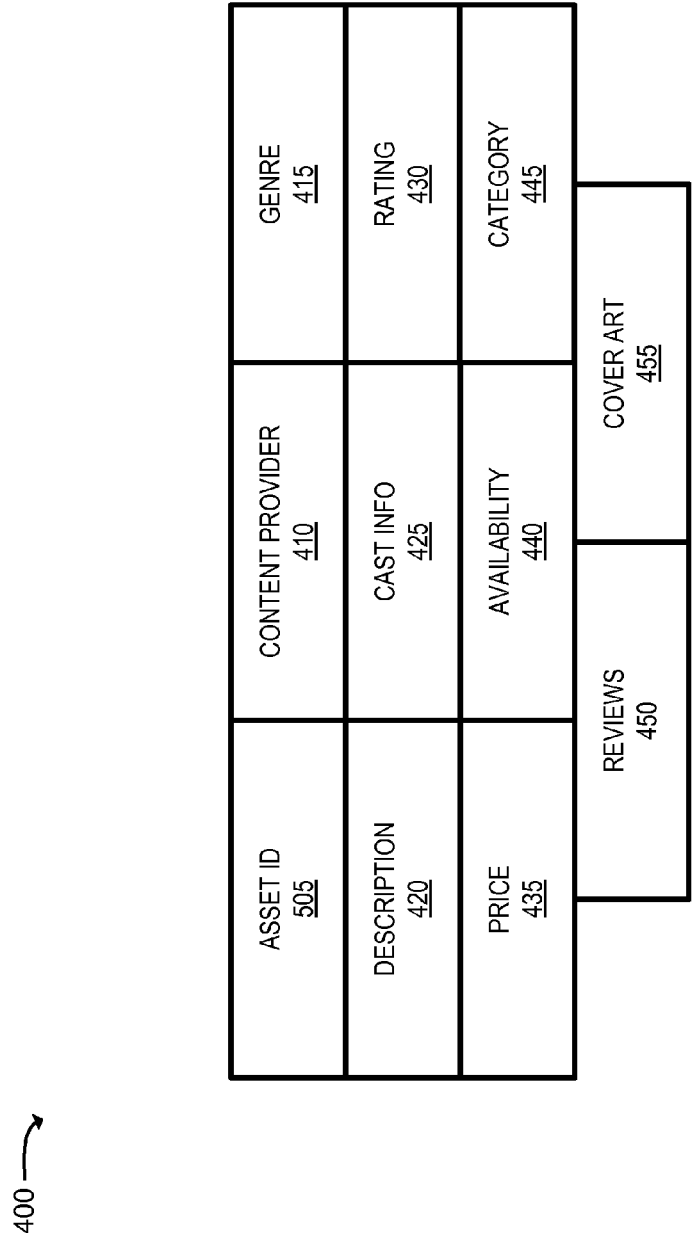
FIG. 4 is a diagram of an example data structure that stores metadata associated with a video asset according to an implementation described herein.

FIG. 4 is a diagram of an example data structure 400 that stores metadata associated with a video asset according to an implementation described herein. Catalog server 235 and/or VOD server 225 may store metadata, associated with video assets that are stored within VOD server 225 and/or CDN server 230, respectively, within data structure 400. Data structure 400 may include a collection of fields, such as an asset identifier (ID) field 405, a content provider field 410, a genre field 415, a description field 420, a cast information (info) field 425, a rating field 430, a price field 435, an availability field 440, a category field 445, a reviews field 450, and a cover art field 455. Data structure 400 includes fields 405-455 for explanatory purposes. In practice, data structure 400 may include additional fields, fewer fields, different fields, or differently arranged fields than are described with respect to data structure 400.

Asset ID field 405 may store a unique identifier (e.g., one or more sequences of characters, a title, etc.) associated with a particular video asset. Content provider field 410 may store information associated with content provider 130 (e.g., a device identifier, a name, etc.) from which the particular video asset was received. Genre field 415 may store information associated with a genre (e.g., drama, history, horror, kids, etc.) that corresponds to the particular video asset. Description field 420 may store a description associated with the particular video asset, such as a summary of a movie when the particular video asset corresponds to the movie. Cast info field 425 may store information associated with an actor, a director, a producer, and/or other individuals associated with the particular video asset.

Rating field 430 may store information associated with a rating (e.g., general audience (G), parental guidance (PG), PG-13, restricted (R), mature audience (MA), etc.) that corresponds to the particular video asset. Price field 435 may store information, associated with one or more prices, that corresponds to the particular video asset. For example, the prices may correspond to a purchase price, a rental price, a subscription price, etc. Availability field 440 may store information associated with an availability of the particular asset. For example, availability field 440 store information that identifies when the particular video asset may be released to user devices 110 and/or when the particular asset is no longer available to be distributed to user devices 110.

Category field 445 may store information associated with a category that corresponds to the particular video asset. The information, associated with the category, may include, for example, an indication that the particular video asset is a movie, a television program, a video game, etc. Reviews field 450 may store information associated with reviews, by users associated with VPS 220 and possibly users not associated with VPS 220, of the particular video asset. The information associated with the reviews may, for example, be represented by one or more symbols, such as a star symbol (e.g., four out of five stars, etc.), a thumbs-up and/or thumbs-down symbol, etc. Cover art field 460 may include one or more images associated with the particular asset.

Figure 5:
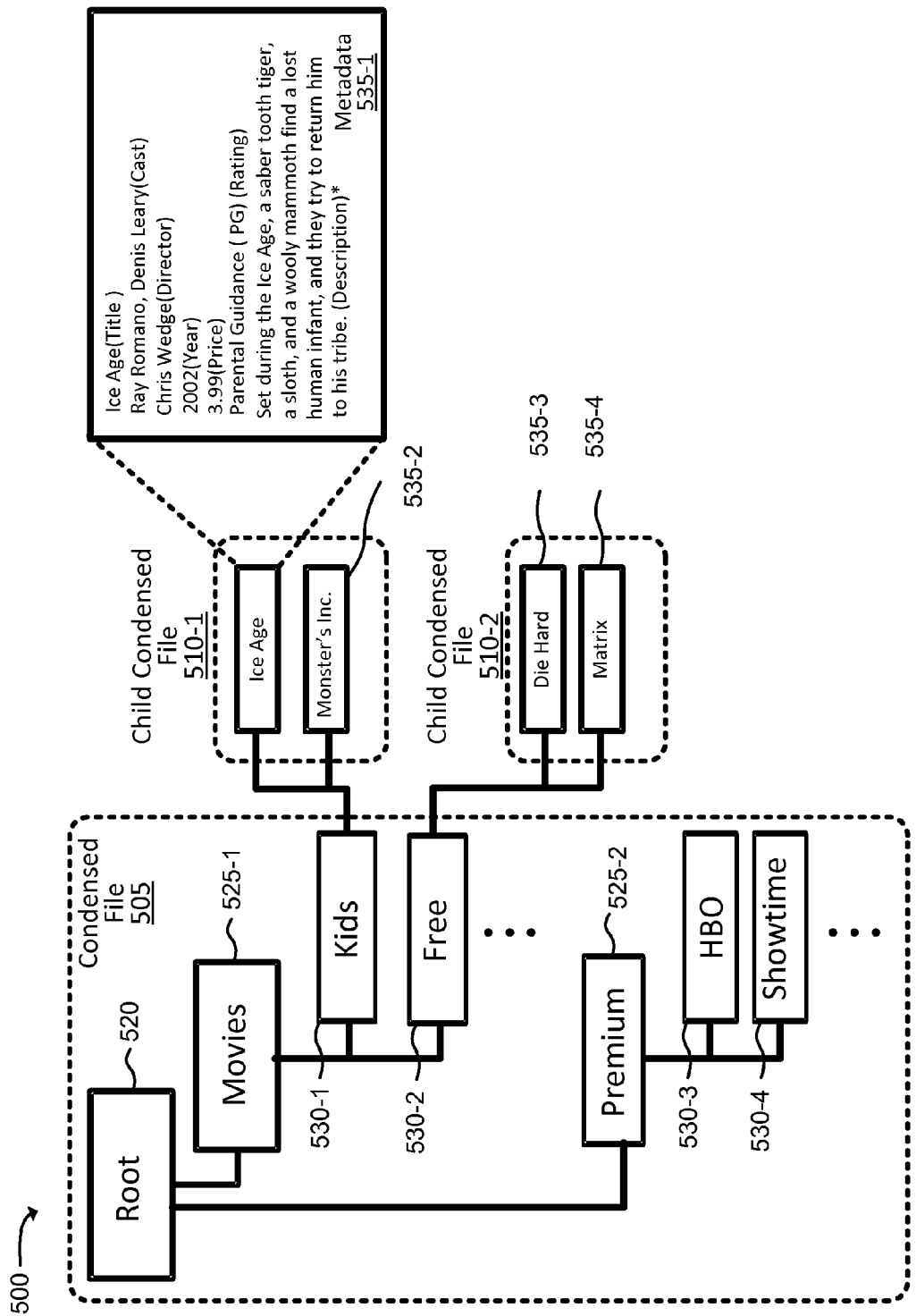
FIG. 5 is a diagram of an example hierarchical data structure according to an implementation described herein.

FIG. 5 is a diagram of an example hierarchical data structure 500 (hereinafter referred to as "structure 500") according to an implementation described herein. Structure 500 may represent a catalog of video assets that are stored by VOD server 225 and/or CDN server 230. Structure 500 may include a condensed file data item 505 (hereinafter referred to as "condensed file 505"), and a pair of child condensed file data items 510-1 and 510-2 (hereinafter referred to collectively as "child condensed files 510" and individually as "child condensed file 510").

Condensed file 505 may represent a condensed file that stores folder information (e.g., information associated with folders and/or subfolders that do not store metadata associated with a video asset). Condensed file 505 may include a root folder data item 520 (hereinafter referred to as "root folder 520"), a pair of folder data items 525-1 and 525-2 (hereinafter referred to collectively as "folders 525" and individually as "folder 525"), and group of subfolder data items 530-1, . . . 530-4 (hereinafter referred to collectively as "subfolders 530" and individually as "subfolder 530"). Root folder 520 may represent a root folder, within a catalog, via which user device 110 may begin a navigation session to access a folder and/or subfolder in order to obtain metadata, associated video assets, that are stored in VPS 120. Root folder 520 may, generally, not be associated with the metadata. For example, a user, of user device 110, may instruct user device 110 to navigate, via root folder 520, to access one or more folders 525 associated with a different categories, genres, sources (e.g., such as content providers 130), ratings, etc., associated with the video assets.

Folder 525 may represent a child folder, relative to root folder 520, that corresponds to a category, genre, source, rating, etc. associated with video assets stored by VPS 120. Folder 525 may generally, not be associated with metadata. However, occasionally, folder 525 may be associated with metadata, in which case, folder 525 may be a leaf folder 525.

User may instruct user device 110 to navigate, via folder 525-1, associated with a category (e.g., such as movies). For example, user device 110 may navigate, via folder 525-1, to access one or more subfolders 530 associated with a subcategory, such as subfolder 530-1 (e.g., kids movies), subfolder 530-2 (e.g., free movies), and/or another subcategory associated with the category. In another example, user device 110 may navigate, via folder 525-2 associated with another category and/or a source, such as premium channels (e.g., shown as "premium"). User device 110 may navigate, via folder 525-2, to access one or more subfolders 530 associated with another subcategory or source, such as subfolder 530-3 (e.g., HBO), subfolder 530-4 (e.g., Showtime), and/or another subcategory or source.

Subfolder 530 may represent a child folder relative to folder 525 or a grandchild folder, relative to root folder 520, that corresponds to a subcategory, subgenre, etc. associated with video assets stored by VPS 120. Subfolder 530 may correspond to a first type of subfolder 530 that is not associated with metadata or a second type of subfolder 530 that is associated with metadata (e.g., a leaf subfolder 530). The first type of subfolder 530 may, for example, permit user device 110 to access another subfolder 530 that is a child folder to subfolder 530 (e.g., not shown in FIG. 5). The other subfolder 530 may likewise be a first type or a second type of subfolder 530.

In another example, a second type of subfolder 530, such as leaf subfolder 530-1, may permit user device 110 to access metadata associated with a video asset. In this example, the user may instruct user device 110 to access leaf subfolder 530-1 to retrieve a video asset associated with a subcategory, such as kids movies. Accessing leaf subfolder 530-1 may cause user device 110 to communicate with BOS 250, via application server 215 and/or IMG server 220, to retrieve child condensed file 510 (e.g., child condensed file 510-1) that corresponds to leaf subfolder 530-1. In another example, user device 110 may access another leaf subfolder 530 associated with free movies (e.g., leaf subfolder 530-2). Accessing leaf subfolder 530-2 may cause user device 110 to communicate with BOS 250 to retrieve another child condensed file 510 (e.g., child condensed file 510-2) that corresponds to leaf subfolder 530-2.

Child condensed file 510 may represent a child condensed file that stores metadata, associated with a video asset, that corresponds to a leaf subfolder 530 identified by condensed file 505. Child condensed file 510-1 may store a pair of metadata data items 535-1 and 535-2. Child condensed file 510-2 may store metadata data items 535-3 and 535-4. Metadata data item 535 may represent all or a portion of the metadata described above with respect to data structure 400 of FIG. 4. For example, metadata 535-1 may include a title associated with a video asset (e.g., ice age), information associated with a cast (e.g., Ray Romano, Denis Leary) and/or director (e.g., Chris Wedge), etc., a time when the video asset was released to the public (e.g., 2002), a price associated with the video asset (e.g., 3.99), a rating associated with the video asset (e.g., parental guidance (PG) and/or a description of the video asset (e.g., set during the ice age, . . . ). In an example implementation, user device 110 may not retrieve child condensed file 510 associated with a rating (e.g., general audience (G), parental guidance (PG), restricted (R), etc.) that is not permitted by parental control settings specified by a user of user device 110.

Structure 500 includes data items 505-535 for explanatory purposes. In practice, structure 500 may include additional data items, fewer data items, different data items, or differently arranged data items than are described with respect to structure 500.

Figure 6:
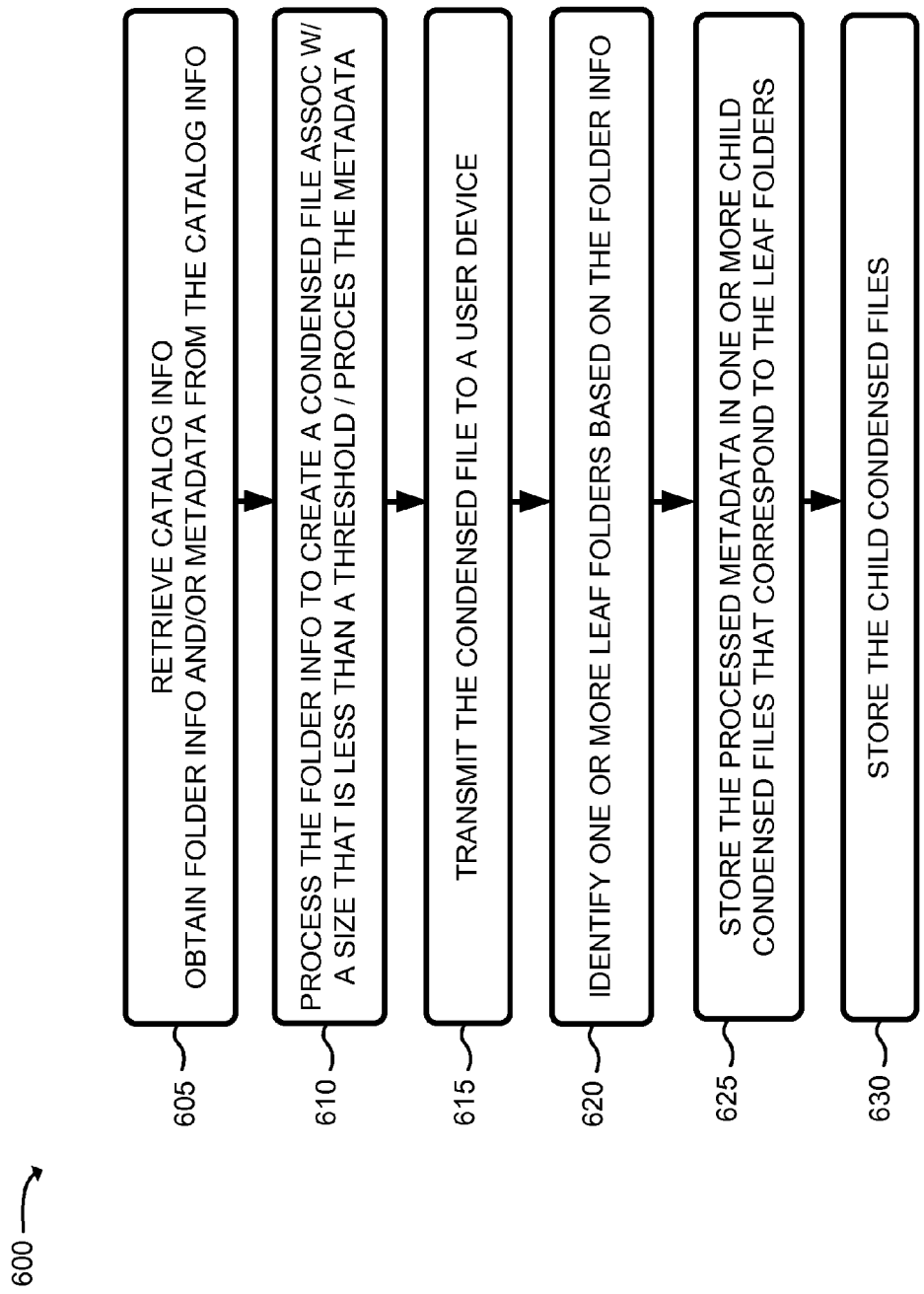
FIG. 6 is a flow chart of an example process for generating condensed files according to an implementation described herein.

FIG. 6 is a flow chart of an example process 600 for generating condensed files according to an implementation described herein. In one example implementation, process 600 may be performed by BOS 250. In another example implementation, some or all of process 600 may be performed by a device, or collection of devices separate from, or in combination with BOS 250.

As shown in FIG. 6, process 600 may include retrieving catalog information and obtaining folder information from the catalog information (block 605). For example, BOS 250 may communicate with VOD server 225 to obtain catalog information associated with video assets that are stored in VOD server 225. BOS 250 may also communicate with catalog server 230 to obtain catalog information associated with video assets that are stored in CDN server 230.

BOS 250 may obtain, from the catalog information, folder information and/or metadata associated with the video assets. The folder information may include information associated with folders and/or subfolders that represent a hierarchical data structure (e.g., such as structure 500 of FIG. 5) associated with the catalog. The folders and/or subfolders may, in a manner similar to that described above with respect to FIG. 5, correspond to categories and/or subcategories associated with video assets stored in VOD server 225 and/or CDN sever 230. For example, a folder may correspond to a category associated with the video assets, such as movies, games, music videos, etc. and may provide access to one or more subfolders that correspond to a subcategory of the category. One of the subfolders may, for example, correspond to video assets associated with horror movies, which is a subcategory of a category, such as movies, associated with the folder. The subfolder may provide access to other subfolders that are associated with other subcategories, such as restricted audience (R)-rated horror movies, parental guidance (PG)-rated horror movies and/or any other grouping of horror movies. The subfolder may also provide access to metadata associated with the video assets associated with the horror movies.

As also shown in FIG. 6, process 600 may include processing the folder information and/or the metadata, and/or storing the processed folder information in a condensed file (block 610). For example, BOS 250 may process the folder information in a manner that reduces a size (e.g., based on a quantity of bits) of the folder information to a level that is less than a threshold. The threshold may be based on a memory allocation (e.g., a quantity of bits of memory), associated with user device 110, that is available to store the folder information.

BOS 250 may use a converter application to process the folder information by converting the folder information from a first format (e.g., based on an American Standard Code for Information Interchange (ASCII) format, an image format, etc.) into a second format (e.g., a binary format, a hex format, etc.) that allows the folder information to be stored, on user device 110, in a manner that conforms to the memory allocation. The converter application may, for example, encode the folder information (e.g., that includes text, images, etc.) into a string of binary characters (e.g., ones and zeros) and/or other characters (e.g., hex characters). The encoded folder information may correspond to a quantity of bits that is less than another quantity of bits associated with the folder information prior to being converted to the second format. The quantity of bits, associated with the encoded folder information, may be less than the threshold.

BOS 250 may use the processed folder information to generate a condensed file that includes the processed folder information. BOS 250 may generate the condensed file based on folder information obtained from catalog information received from VOD server 225. BOS 250 may generate another condensed file based on other folder information obtained from other catalog information received from catalog server 235.

BOS 250 may also process all or a portion of the metadata in a manner that reduces a size associated with the metadata. For example, BOS 250 may compress the metadata and/or a portion of the metadata, such as a description of a video asset, an image associated with the video asset, etc. BOS 250 may, for example, compress the metadata or the portion of the metadata using a compression application (e.g., ZIP, Phil Katz ZIP (PKZIP), GZIP, PNG, etc.) hosted by BOS 250. In another example, BOS 250 may use the converter application, in a manner similar to that described above, to convert the metadata to another format. Reducing the size of the metadata may reduce a quantity of time and/or bandwidth utilized to transmit the metadata to user device 110 (e.g., in response to a request for the metadata, etc.).

As further shown in FIG. 6, process 600 may include transmitting the condensed file to a user device (block 615) and identifying one or more leaf folders based on the folder information (block 620). For example, BOS 250 may transmit the condensed file to the set top box user device 110 via IMG server 220. The set top box user device 110 may receive the condensed file and may store the condensed file. In another example, the set top box user device 110 may receive the condensed file and may remove, erase, and/or over-write a previous version of the condensed file. The set top box user device 110 may obtain the folder information from the condensed file and may render one or more folders and/or subfolders, based on the folder information, for display on a display device associated with set top box user device 110. BOS 250 may also transmit another condensed file to user device 110 via application server 215. User device 110 may receive the other condensed file and may store the other condensed file. In another example, user device 110 may receive the condensed file and may remove, erase, and/or over-write a previous version of the condensed file. User device 110 may obtain the other folder information from the other condensed file and may render one or more folders and/or subfolders, based on the other folder information, for display on user device 110.

BOS 250 may identify one or more leaf folders that are included in the catalog based on information associated with one or more leaf folders that is included in the folder information. The information associated with the leaf folders may include an indication that a child condensed file is to be retrieved when the leaf folders are accessed.

As yet further shown in FIG. 6, process 600 may include storing processed metadata in one or more child condensed files that correspond to the one or more leaf folders (block 625) and store the child condensed files (block 630). For example, BOS 250 may generate a child condensed file for each of the one or more leaf folders that are identified by the folder information. BOS 250 may, for example, store metadata, that corresponds to a particular leaf folder, in a child condensed file that corresponds to the particular leaf folder. BOS 250 may store the metadata in other child condensed files that correspond to the leaf folders. BOS 250 may store the child condensed files in a memory associated with BOS 250.

Figure 7:
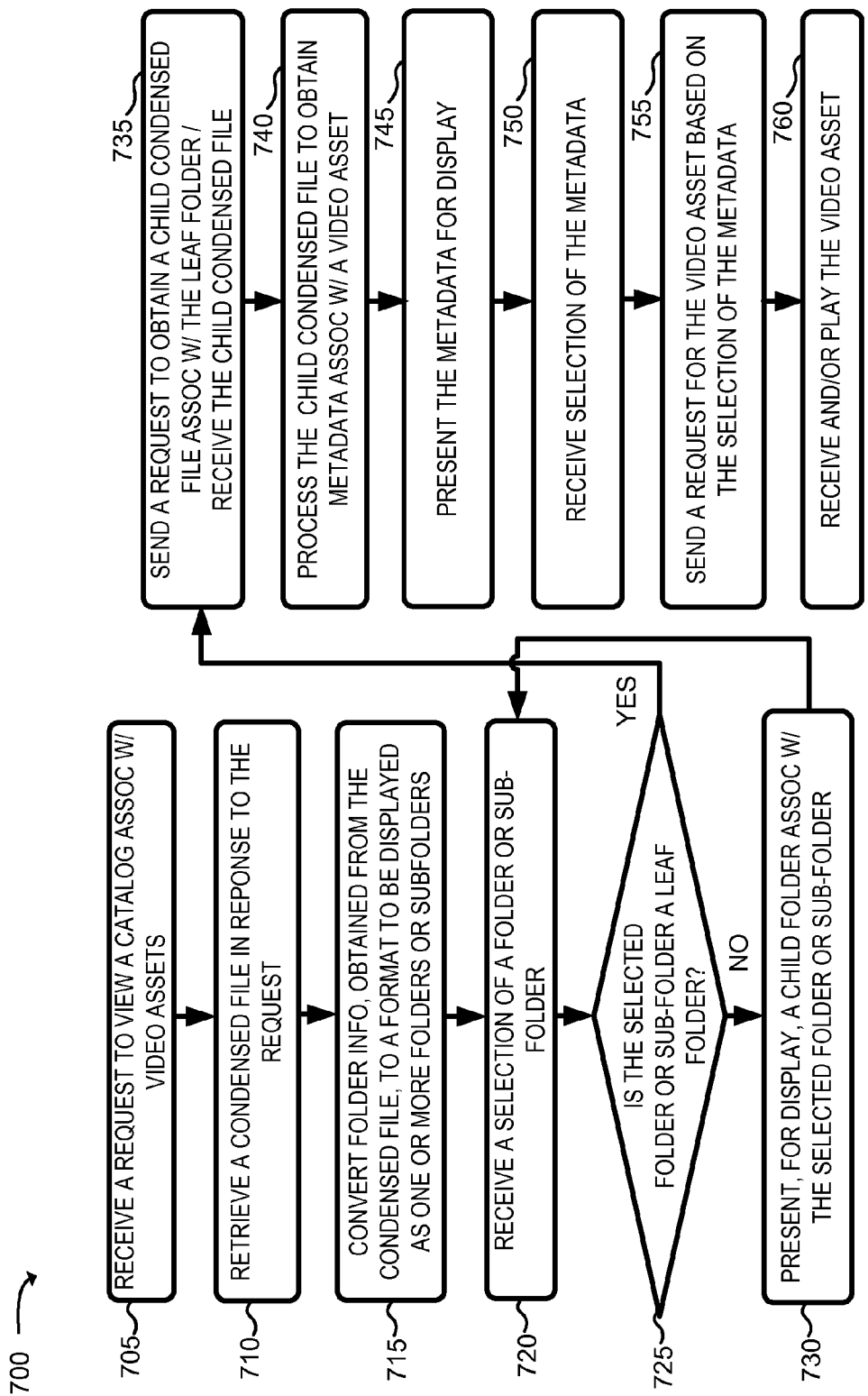
FIG. 7 is a flow chart of an example process for using a condensed file according to an implementation described herein.

FIG. 7 is a flow chart of an example process 700 for using a catalog condensed file according to an implementation described herein. In an example implementation, process 700 may be performed by user device 110. In another example implementation, some or all of process 700 may be performed by a device, or collection of devices separate from, or in combination with user device 110.

As shown in FIG. 7, process 700 may include receiving a request to display a catalog associated with one or more video assets (block 705) and retrieving a condensed file in response to the request (block 710). For example, a user, of user device 110, may desire to view a catalog via which metadata, associated with one or more video assets, can be accessed. The user may instruct user device 110 to display the catalog on user device 110.

User device 110 may receive the request and may retrieve, from a memory associated with user device 110, a condensed file, such as condensed file 505 (FIG. 5), that stores folder information associated with the catalog. The folder information may identify folders 525 and/or subfolders 530 that form the logical structure of the catalog in a manner similar to that described above in FIG. 5.

As also shown in FIG. 7, process 700 may include converting folder information, obtained from the condensed file, to a format that can be displayed as one or more folders or subfolders (block 715). For example, user device 110 may obtain all or a portion of the folder information from condensed file 505. User device 110 may process the folder information to convert the folder information to a format that can be displayed on user device 110 and/or a display associated with user device 110. For example, user device 110 may convert all or a portion of the folder information (e.g., that corresponds to root folder 520 and/or one or more folder 525 and/or subfolders 530) from a particular format (e.g., a binary format) to another format (e.g., a hypertext markup language (HTML) format, or some other format). User device 110 may present the processed folder information for display. The processed folder information, when displayed, may include one or more folders 525, associated with root folder 520, of the catalog. In another example implementation, the processed folder information may include folders 525 and/or one or more subfolders 530, associated with folders 525.

As further shown in FIG. 7, process 700 may include receiving a selection of a folder or subfolder (block 720). For example, the user may instruct user device 110 to select a particular folder 525 to access one or more subfolders 530. In another example, the user may instruct user device 110, to select a particular subfolder 530 without first selecting one of folders 525 (e.g., when the displayed folder information includes both folders 525 and subfolders 530). User device 110 may receive the instruction and may select folder 525 and/or subfolder 530.

As yet further shown in FIG. 7, if the selected folder or subfolder is not a leaf folder (block 725—NO), then process 700 may include presenting, for display, one or more child folders associated with the selected folder or subfolder (block 730). For example, user device 110 may determine whether the selected folder 525 or subfolder 530 is associated with metadata. In one example, user device 110 may determine that the selected folder 525 or subfolder 530, is a leaf folder by determining whether the selected folder 525 or subfolder 530 includes an indication that a child condensed file, such as child condensed file 510, is to be retrieved from VPS 120.

Based on a determination that the selected folder 525 or subfolder 530 does not include the indication that child condensed file 510 is to be retrieved, user device 110 may present, for display, folder information that corresponds to one or more child folders associated with selected folder 525 or subfolder 530. User device 110 may present, for display, the folder information without communicating with VPS 120 to obtain additional folder information. The child folders may represent other subfolders 530 relative to folder 525 when folder 525 is the selected folder. In another example, the child folders may represent other subfolders 530, relative to subfolder 530, when subfolder 530 is the selected subfolder 530. The user may instruct user device 110 to select one of the other subfolders 530 and user device 110 may receive the selection. User device 110 may determine whether the selected other subfolder 530 is a leaf folder in a manner similar to that described above (e.g., with respect to blocks 720 and 725).

As still further shown in FIG. 7, if the selected folder or subfolder is a leaf folder (block 725—YES), then process 700 may include sending a request to obtain a child condensed file, associated with the leaf folder, and receiving the child condensed file (block 735). For example, user device 110 may identify selected folder 525 and/or subfolder 530, as the leaf folder, based on a determination that the selected folder 525 and/or subfolder 530 includes the indication that the child condensed file, such as child condensed file 510, is to be retrieved from VPS 120. Based on the determination that the selected folder 525 and/or subfolder 530 includes the indication that child condensed file 510 is to be retrieved, user device 110 may transmit a request, to BOS 250, to obtain child condensed file 510 that corresponds to the selected folder 525 and/or subfolder 530.

For example, if user device 110 is a set top box user device 110, the request may be transmitted to BOS 250 via IMG server 220. In another example, if user device 110 is a type of user device 110 that is a different type of user device 110 than a set top box (e.g., a computer user device 110, wireless handheld user device 110, gaming user device 110, etc.), then the request may be transmitted to BOS 250 via application server 215. The request may include information (e.g., an identifier) associated with the selected folder 525 and/or subfolder 530, and/or information (e.g., another identifier) associated with child condensed file 510 that corresponds to the selected folder 525 and/or subfolder 530.

BOS 250 may receive the request and may retrieve child condensed file 510, from a memory associated with BOS 250 in response to the request. BOS 250 may transmit child condensed file 510 to user device 110 via IMG server 220 (e.g., when user device 110 is a set top box user device 110) and/or via application server 215 (e.g., when user device 110 is the different type of user device 110). User device 110 may receive child condensed file 510 from BOS 250.

In another example implementation, user device 110 may not transmit the request to obtain child condensed file 510 based on a determination that child condensed file 510 is associated with a rating (e.g., general audience (G), parental guidance (PG), restricted (R), etc.) that is not permitted by parental control settings specified by a user of user device 110.

As also shown in FIG. 7, process 700 may include processing the child condensed file to obtain metadata associated with a video asset (block 740) and presenting the metadata for display (block 745). For example, user device 110 may obtain, from child condensed file 510, metadata associated with a video asset. In another example, child condensed file 510 and/or the metadata may have been previously compressed (e.g., by BOS 250 when creating child condensed file 510), which may cause user device 110 to process child condensed file 510 by expanding and/or uncompressing the child condensed file 510 and/or the metadata. User device 110 may render the processed metadata for display on user device 110 and/or a display device associated with user device 110.

In another example implementation, user device 110 may not render the processed metadata for display based on a determination that child condensed file 510 is associated with a rating (e.g., general audience (G), parental guidance (PG), restricted (R), etc.) that is not permitted by parental control settings specified by a user of user device 110.

As further shown in FIG. 7, process 700 may include receiving selection of the metadata (block 750) and sending a request for the video asset based on the selection of the metadata (block 755). For example, the user may instruct user device 110 to select the metadata and user device 110 may, in response to the instruction, select the metadata. User device 110 may, based on the selection of the metadata, transmit a request, to IMG server 220 (e.g., when user device 110 is a set top box user device 110) or to application server 215 (e.g., when user device 110 is the other type of user device 110), for the video asset. The request may include the metadata associated with the video asset.

As yet further shown in FIG. 7, process 700 may include receiving and/or playing the video asset (block 760). For example, IMG server 220 may receive the request and may communicate with VOD server 225 to cause VOD server 225 to transmit the video asset, to which the metadata corresponds, to set top box user device 110. Set top box user device 110 may receive the video asset and may play the video asset on set top box user device 110. In another example, application server 215 may receive the request and may communicate with CDN server 230 to cause CDN server 230 to transmit the video asset, to which the metadata corresponds, to user device 110 that is the different type of user device 110. User device 110 may receive the video asset and may play the video asset on user device 110.

Systems and/or methods, described herein, may allow a user device to navigate via a hierarchical data structure, associated with a catalog of assets that are stored within a video provisioning system, without making repeated data calls, through the network, for additional information associated with the hierarchical data structure. Enabling the user device to navigate through the hierarchical data structure, without making the repeated data calls through the network, may reduce a quantity of time and/or bandwidth utilization associated with rendering the hierarchical data structure, on the user device, which may improve a user experience for a user of the user device.

The foregoing description provides illustration and description, but is not intended to be exhaustive or to limit the implementations to the precise form disclosed. Modifications and variations are possible in light of the above teachings or may be acquired from practice of the embodiments.

While series of blocks have been described with respect to FIGS. 6 and 7, the order of the blocks may be modified in other implementations. Further, non-dependent blocks may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method performed by a server device, associated with a video provisioning system (VPS), the method comprising:
receiving data indicating a hierarchical representation of categories and subcategories associated with a catalog of video assets via the VPS;
creating a first file that includes the data indicating the hierarchical representation of the categories and the subcategories, wherein the first file does not include metadata associated with the video asset; and
transmitting the first file to a set top box.

2. The method of claim 1, where creating the first file, further includes:
processing the data indicating the hierarchical representation of the categories and the subcategories in a manner that reduces a quantity of bits, of the data indicating the hierarchical representation of the categories and the subcategories, to a level that is less than a threshold.

3. The method of claim 2, where the threshold corresponds to another quantity of bits associated with an allocated memory, in the set top box, that is available to store the processed data indicating hierarchical representation of the categories and the subcategories.

4. The method of claim 1, where creating the first file, further includes:
converting the data indicating the hierarchical representation of the categories and the subcategories from a first format to a second format, where:
the first format is associated with a first quantity of bits, and
the second format is associated with a second quantity of bits that is less than a threshold for an allocated memory, associated with the set top box, that is available to store the first file, and where the threshold is less than the first quantity of bits.

5. The method of claim 1, where the hierarchical representation of the categories and the subcategories includes a plurality of categories associated with the video assets,
- where each of the plurality of categories corresponds to a respective different portion of the video assets,
- where at least one of the plurality of categories is associated with one or more subcategories associated with one of the portions of the video assets, and
- where at least one of the one or more subcategories is associated with metadata associated with a video asset.

6. The method of claim 1, further comprising:
- receiving, from the set top box, a request for metadata associated with a video asset, where the request includes an identifier associated with a category or subcategory, within the hierarchical representation of the categories and the subcategories;
- identifying a second file that corresponds to the identifier associated with the category or subcategory;
- retrieving, from a memory associated with the server device, the second file, where the second file includes the metadata associated with the video asset; and
- transmitting the second file to the set top box, where transmitting the second file to the set top box allows the set top box to obtain the metadata from the second file.

7. The method of claim 6, further comprising:
- receiving, from the set top box, the metadata associated with the video asset; and
- transmitting the video asset to the set top box based on the metadata received from the video asset.

8. The method of claim 1, further comprising:
- receiving metadata associated with the video assets;
- determining a manner in which each of the video assets are associated with each category and subcategory within the hierarchical representation of the categories and the subcategories; and
- store the metadata in a plurality of other files based on the manner in which each of the video assets are associated with each category and subcategory, of the categories and the subcategories.

9. The method of claim 8, where storing the metadata in the plurality of other files further includes:
- compressing all or a portion of the metadata; and
- storing the compressed metadata in the plurality of other files.

10. The method of claim 1, where creating the first file includes:
- converting the data indicating the hierarchical representation of the categories and the subcategories into a binary file, where the binary file enables the set top box to render, for display, all or a portion of the hierarchical representation of the categories and the subcategories without communicating with the VPS.

11. A set top box comprising:
- a memory to store a first file that includes data indicating a hierarchical representation of categories and subcategories associated with a catalog of video assets stored in a network, wherein the first file does not include metadata associated with the video asset; and
- a processor to:
  - receive a request to display the catalog,
  - retrieve the data indicating the hierarchical representation of the categories and the subcategories from the first file stored in the memory,
  - process the data indicating the hierarchical representation of the categories and the subcategories, where processing the data indicating the hierarchical representation of the categories and the subcategories enables the hierarchical representation of the categories and the subcategories to be displayed in a format that can be understood, when displayed on a monitor associated with the set top box, by a user of the set top box,
  - present, for display and without communicating with the network, all or a portion of the processed data indicating the hierarchical representation of the categories and/or the subcategories, and
  - retrieve, from the network and in response to a selection of a category or subcategory of the processed the data indicating hierarchical representation of the categories and the subcategories, a second file associated with the selected category or subcategory, where the second file includes metadata, associated with a video asset, that allows the set top box to obtain the video asset.

12. The set top box of claim 11, where the processor is further to:
- receive, from the network, the data indicating the hierarchical representation of the categories and the subcategories, and
- store, in the memory, the data indicating the hierarchical representation of the categories and the subcategories, where storing the data indicating the hierarchical representation of the categories and the subcategories includes erasing or over-writing a previous version of the hierarchical representation of the categories and the subcategories.

13. The set top box of claim 11, where the processor is further to:
- decompress the data indicating the hierarchical representation of the categories and the subcategories, where decompressing the data indicating the hierarchical representation of the categories and the subcategories allows the hierarchical representation of the categories and the subcategories to be processed.

14. The set top box of claim 11, where the memory stores the hierarchical representation as a binary file.

15. The set top box of claim 11, where the processor is further to:
- receive one or more instructions to select one or more categories or subcategories, of the hierarchical representation of the categories and the subcategories, and
- provide, in response to the one or more instructions, information relating to the selected one or more categories or subcategories, where the information relating to each of the selected one or more categories is provided without communicating with the network to obtain the information relating to each of the selected one or more categories or subcategories.

16. The set top box of claim 11, where, when retrieving the second file associated with the selected category or subcategory, the processor is further to:
- process the second file that corresponds to the selected category or subcategory, where processing the second file enables metadata to be presented for display in another format that can be understood by the user, and
- retrieve, from the network and in response to selection of the metadata, a video asset with which the selected metadata corresponds.

17. The set top box of claim 16, where, when processing the second file, the processor is further to:
- decompress the second file, where decompressing the second file converts the metadata into the other format or allows the metadata to be obtained from the second file.

18. A user device comprising:
a memory to store a first file that includes data indicating a hierarchical representation of categories and subcategories associated with a catalog of video assets stored in a network, wherein the first file does not include metadata associated with the video asset; and
a processor to:
   receive a request to display the catalog,
   retrieve the data indicating the hierarchical representation of the categories and the subcategories from the first file stored in the memory,
   present, for display and without communicating with the network, all or a portion of a plurality of categories or subcategories associated with the hierarchical representation of the categories and the subcategories in response to the request,
   receive selection of a category or subcategory, of the presented all or the portion of the plurality of categories or subcategories, and
   retrieve, in response to the selection of the category or subcategory and from the network, a second file associated with the selected category or subcategory, where the second file includes metadata, associated with a video asset, that allows the user device to obtain the video asset.

19. The user device of claim 18, where the processor is further to:
   convert the data indicating the hierarchical representation of the categories and the subcategories to a format that, when displayed, can be understood by a user of the user device.

20. The user device of claim 19, where when converting the data indicating the hierarchical representation of the categories and the subcategories to the format, the processor is to:
   convert the data indicating the hierarchical representation of the categories and the subcategories from a first format to a second format,
      where the first format corresponds to a binary format or a hex format, and
      where the second format corresponds to a type of format that is different than the binary format or the hex format.

21. The user device of claim 18, where the processor is further to:
   receive an instruction to select one category or subcategory, of the plurality of categories or subcategories, where the selected one category or subcategory does not include metadata associated with the video asset, and
   provide, in response to the instruction, information relating to the selected one category or subcategory without communicating with the network to obtain the information related to the selected one category or subcategory.

22. The user device of claim 18, where, when retrieving the second file associated with the selected category or subcategory, the processor is further to:
   transmit, to the network, a request for the second file associated with the selected category or subcategory, where the request for the second file includes the selected category or subcategory,
   receive, from the network, the second file associated with the selected category or subcategory,
   decompress the second file, associated with the selected category or subcategory, to obtain the metadata from the second file associated with the selected category or subcategory, and
   retrieve the video asset using the metadata obtained from the second file, associated with the category or subcategory, that permits the user device to play the video asset.

23. The user device of claim 22, where, when decompressing the second file associated with the selected category or subcategory, the processor is further to:
   convert the metadata to a format that, when displayed by the user device, can be understood by a user of the user device,
   present, for display, the converted metadata, and
   receive a selection of the presented metadata, where the selection of the presented metadata includes an instruction for the user device to retrieve, from the network, a video asset with which the presented metadata is associated.

24. The user device of claim 18, where the user device is a type of user device that corresponds to a set top box.

25. The user device of claim 18, where the processor is further to:
   determine that the metadata includes information associated with a rating that is not permitted by parental controls that are specified by a user of the user device, and
   present, for display, a notification that the video asset cannot be obtained based on the determination that the metadata includes the information associated with the rating that is not permitted by the parental controls.

* * * * *